(12) United States Patent
Matsumoto et al.

(10) Patent No.: US 6,410,034 B1
(45) Date of Patent: Jun. 25, 2002

(54) DERMAL ABSORPTION-PROMOTING AGENT

(75) Inventors: Mitsuo Matsumoto; Makiko Fujii; Yasuhiro Takeda; Minuro Hanada, all of Tokyo (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/388,482

(22) Filed: Sep. 2, 1999

(30) Foreign Application Priority Data

Sep. 3, 1998 (JP) .......................................... 10-265652
Oct. 1, 1998 (JP) .......................................... 10-294455

(51) Int. Cl.$^7$ ............................. A61K 7/00; A61K 6/00; A01N 31/08
(52) U.S. Cl. ...................... 424/401; 424/401; 424/403; 424/405; 514/729; 514/724; 514/738; 514/739; 514/827; 514/828; 514/829; 514/830; 514/844; 514/889; 514/918
(58) Field of Search .............................. 514/729, 724, 514/738, 739, 827, 828, 829, 830, 844, 885, 918; 424/401, 403, 405

(56) References Cited

U.S. PATENT DOCUMENTS 5,681,549 A * 10/1997 McLaughlin et al. ......... 424/54
5,698,209 A * 12/1997 Shono et al. ................ 424/405
5,725,865 A * 3/1998 Mane et al. ................. 424/401
5,725,874 A * 3/1998 Oda et al. ................... 424/443
6,130,255 A * 10/2000 Ikemoto et al. ............. 514/729
6,194,468 B1 * 2/2001 Hattori et al. ............... 514/729
6,328,982 B1 * 12/2001 Shiroyama et al. ......... 424/401

FOREIGN PATENT DOCUMENTS

JP  05294828 A2 * 11/1993
JP  06040875 A2 *  2/1994

OTHER PUBLICATIONS

Fujii et al, Yakuzaigaku 1996, 56(3), 149–155 (abstract).*

JP 06040875, Feb. 15, 1994 (abstract copy from Derwent).*

* cited by examiner

Primary Examiner—Russell Travers
Assistant Examiner—Shahnam Sharareh
(74) Attorney, Agent, or Firm—Kubovcik & Kubovcik

(57) ABSTRACT

A dermal absorption-promoting agent comprising p-methane-3,8-diol and 1,3-butylene glycol as well as a topical formulation containing the same; and a dermal absorption-promoting agent further comprising 1,3-butylene glycol, as well as a topical formulation containing such dermal absorption-promoting agents.

16 Claims, 4 Drawing Sheets

DERMAL ABSORPTION-PROMOTING AGENT

BACKGROUND OF THE INVENTION

1. Field of the Invention

The present invention relates to a dermal absorption-promoting agent comprising p-menthane-3,8-diol and 1,3-butylene glycol as well as a topical formulation containing the same.

The invention also relates to a dermal absorption-promoting agent comprising p-menthane-3,8-diol and 3-l-menthoxypropane-1,2-diol and a dermal absorption-promoting agent further comprising 1,3-butylene glycol, as well as a topical formulation containing such dermal absorption-promoting agents.

2. Prior Art p-Menthane-3,8-diol is a substance contained in an eucalyptus plant, and is known to have a repelling effect on a mosquito. For example, each of Japanese Examined Patent Application Publication (JP-B) No. 3-80,138 and Japanese Patent Application Laid-Open (JP-A) No. 2-250,802 discloses a hazardous organism-repelling agent whose active ingredient is p-menthane-3,8-diol or a derivative thereof. In addition, each of Japanese Patent Application Laid open Nos. 5-294,828 and 6-40,875 discloses a dermal topical formulation which contains p-menthane-3,8-diol and whose repelling effect is sustained for a prolonged period, the latter disclosing a formulation having a further sustained repelling action when p-menthane-3,8-diol is combined with an anti-inflammatory agent and/or an antihistamic agent.

When a drug is administered dermally, it has several advantageous characteristics by which the disadvantages associated with an oral administration or an injection is intended to be overcome. For example, a dermal administration allows a drug to be absorbed directly from a capillary vessel on a skin surface, thus avoiding a first pass effect in the liver and reducing side effects.

Such skin-penetrating property suitable for dermal administration is not possessed by all drugs, and it is required, when applying a dermal absorption system, to take a skin penetrating effect, skin compatibility and clinical demand into consideration. In addition, consideration of a combination with a substance having a dermal absorption-promoting effect for the purpose of promoting the skin penetration of a drug may also be required for exerting the efficacy of the drug.

Various substances having such dermal absorption-promoting effect are known and have been employed. For example, a safety test of a dermal absorption-promoting agent on the skin revealed that the dermal permeation of isosorbide dinitrate in an aqueous suspension was promoted greatly when combined with a monoterpene l-menthol, terpineol or 1,8-cineol (Fragrance Journal, p34, 1996-4). A journal "YAKUZAIGAKU" (vol.56, No.3 (1996) and DDS (Drug Delivery System, Vol. 12, No. 2 (1997)) also stated that l-menthol or 3-l-menthoxypropane-1,2-diol, when combined together with indomethacin, promotes the dermal absorption of indomethacin.

While l-menthol has already been known to promote the dermal absorption of a drug, it has a cool mint flavor, which may sometimes be too intense. On the other hand, 3-l-menthoxypropane-1,2-diol has a p-menthane structure similarly to l-menthol, and is a colorless, odorless, viscous liquid material formed by attaching a glycerin via an ether bond to the hydroxyl group of l-menthol, but its dermal permeation-promoting effect is somewhat lower than that of l-menthol. Nevertheless, since l-menthol and 3-l-menthoxypropane-1,2-diol have less formulation base selectivities and can be combined not only with hydrophilic formulation bases but also with lipophilic formulation bases, they are capable of being applied widely in the field of topical formulations, thus providing high utilities.

SUMMARY OF THE INVENTION

While both of l-menthol and 3-l-menthoxypropane-1,2-diol have p-menthane structures as described above, l-menthol, when employed in preparing a topical formulation, poses a complicated operation during a manufacturing process in order to suppress the too intensive mint flavor. In addition, a residual characteristic mint flavor in a pharmaceutical product makes the product less favorable for users.

On the other hand, 3-l-menthoxypropane-1,2-diol does not have a satisfactory dermal permeation-promoting ability, although it poses no flavor problems.

We made an effort in a study based on the fact that p-menthane-3,8-diol, which is extracted and collected from an eucalyptus plant and has a repelling effect on a mosquito, has a p-menthane structure similarly to l-menthol and 3-l-menthoxypropane-1,2-diol and finally discovered that p-menthane-3,8-diol has a dermal absorption-promoting effect, thus establishing the present invention.

Thus, the present invention provides a dermal absorption-promoting agent comprising p-menthane-3,8-diol and 1,3-butylene glycol as well as a topical formulation containing the same.

The invention also provides a dermal absorption-promoting agent comprising p-menthane-3,8-diol and 3-l-menthoxypropane-1,2-diol and a dermal absorption-promoting agent further comprising 1,3-butylene glycol, as well as a topical formulation containing such dermal absorption-promoting agents.

Figure 1:
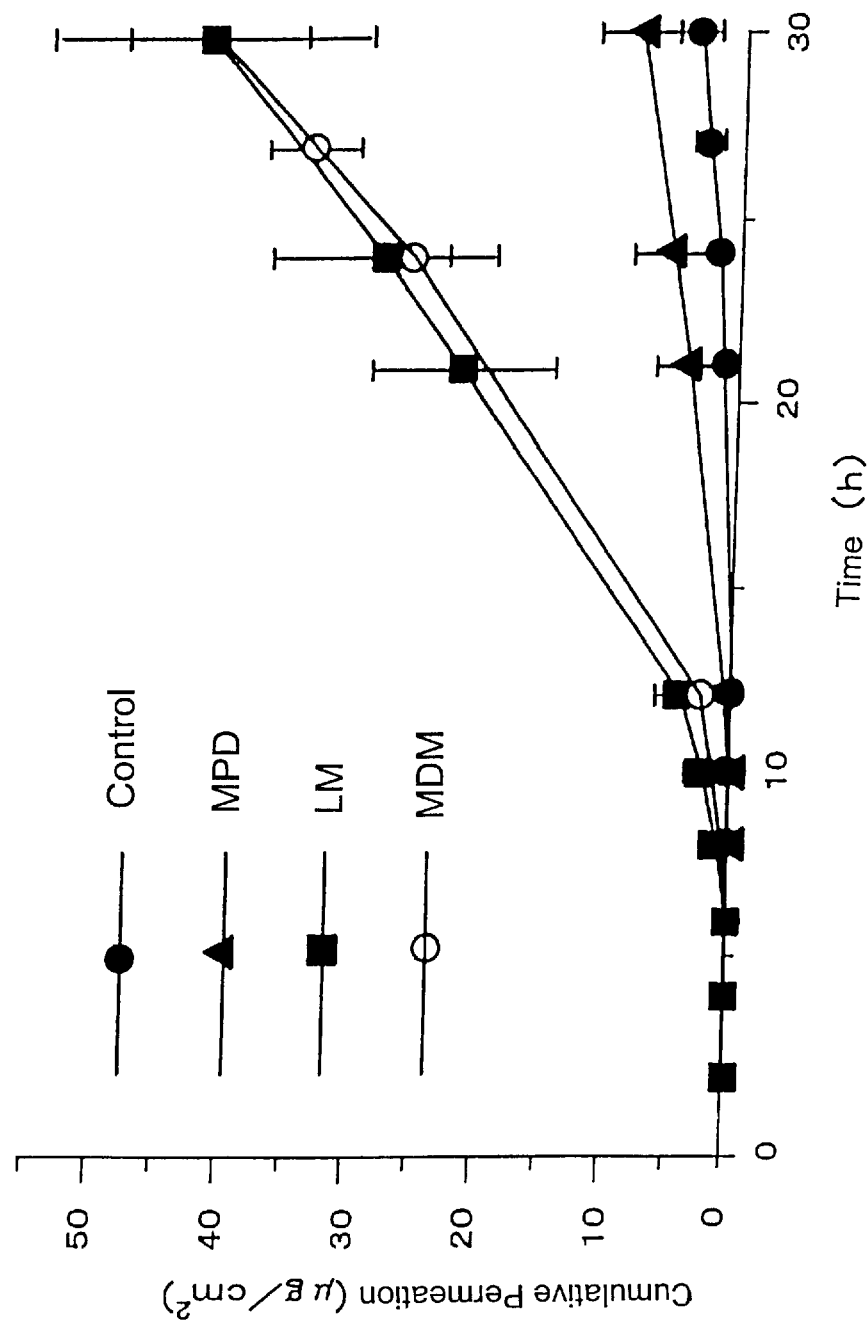
FIG. 1 shows the results of the dermal permeation test of indomethacin (IM) in Example 1.

DETAILED DESCRIPTION OF THE INVENTION p-Menthane-3,8-diol employed in the present invention is a colorless, odorless and viscous material, and exists as any of four isomers, namely, (+)-cis-p-menthane-3,8-diol, (−)-cis-p-menthane-3,8-diol, (+)-trans-p-menthane-3,8-diol and (−)-trans-p-menthane-3,8-diol. This substance usually exists as a mixture of a cis form and a trans form, and may be used in the invention as the mixture, but any of the isomers listed above can appropriately be selected for use.

3-l-menthoxypropane-1,2-diol employed in the present invention may be any of those commercially available.

While various solvents such as ethanol and 1,3-butylene glycol are used in formulating a dermal absorption-promoting agent according to the invention, a low irritating solvent 1,3-butylene glycol is preferred in view of safety.

A dermal absorption-promoting agent according to the invention is used as an auxiliary agent for promoting the dermal absorption of a certain drug contained as an active ingredient in a topical formulation, and is incorporated into a formulation base. The amount to be used may vary appropriately depending on the intended uses and the formulation characteristics (dosage forms).

Thus, p-menthane-3,8-diol may be used as a dermal absorption-promoting agent, in an amount which may vary depending on the intended uses and the formulation characteristics, within a range of 0.1 to 50% by weight, preferably 1 to 10% by weight, for a complete topical formulation. An amount less than 0.1% by weight results in insufficient absorption of a drug through the skin, while an amount exceeding 50% by weight results in a disadvantage such as an excessively rapid absorption of a drug or a fluctuation in an absorption rate.

Also when a dermal absorption-promoting agent comprising both p-menthane-3,8-diol and 3-l-menthoxypropane-1,2-diol is employed, the amount to be employed may be similar to that when p-menthane-3,8-diol is employed. In this case, p-menthane-3,8-diol and 3-l-menthoxypropane-1,2-diol are incorporated in a ratio of 1:99 to 99:1 by weight, preferably 10:90 to 90:10 by weight.

In addition to an active ingredient, auxiliary agents and carriers used customarily in this field including excipients and additives may appropriately be selected and employed in combination. A dermal absorption-promoting agent comprising p-menthane-3,8-diol or p-menthane-3,8-diol together with 3-l-menthoxypropane-1,2-diol can be appropriately used in combination with a drug capable of being administered dermally. Such drug is not particularly limited and may include non-steroidal anti-inflammatory agents such as indomethacin, phenylbutazone, naproxen and ibuprofen as well as antipyretics/analgesics such as antipyrine.

A dosage form of a topical formulation prepared according to the invention is not particularly limited as long as it can be pharmaceutically used, and may include solutions, ointments, creams, sprays, lotions, gels, sols, aerosols, plasters, tapes and the like.

EXAMPLES

The present invention is described in further detail in the following examples, which are not intended to restrict the invention.

Example 1

A lipophilic agent indomethacin (IM) and a hydrophilic agent antipyrine (ANP) were used to compare the dermal absorption-promoting effect of p-menthane-3,8-diol (MDM: mixture of trans and cis forms) with those of l-menthol (LM) and 3-l-menthoxypropane-1,2-diol (MPD) together with a control.

Methods
(1) Sample Preparation
According to the formulations shown in Table 1 (IM) and Table 2 (ANP), each of the three dermal absorption-promoting agents was employed, dissolved in ethanol and combined with water to prepare a sample. The samples thus prepared were stored at 37° C. until use.

TABLE 1

|  | Control | MDM | MPD | LM |
| --- | --- | --- | --- | --- |
| Water (ml) | 6.0 | 6.0 | 6.0 | 6.0 |
| Ethanol (ml) | 4.0 | 4.0 | 4.0 | 4.0 |

TABLE 1-continued

|  | Control | MDM | MPD | LM |
| --- | --- | --- | --- | --- |
| IM (g) | 0.05 | 0.05 | 0.05 | 0.05 |
| MDM (g) | — | 0.3 | — | — |
| MPD (g) | — | — | 0.3 | — |
| LM (g) | — | — | — | 0.3 |

TABLE 2

|  | Control | MDM | MPD | LM |
| --- | --- | --- | --- | --- |
| Water (ml) | 6.0 | 6.0 | 6.0 | 6.0 |
| Ethanol (ml) | 4.0 | 4.0 | 4.0 | 4.0 |
| ANP (g) | 0.2 | 0.2 | 0.2 | 0.2 |
| MDM (g) | — | 0.3 | — | — |
| MPD (g) | — | — | 0.3 | — |
| LM (g) | — | — | — | 0.3 |

(2) Dermal Permeation Test
A skin of Yucatan Micropig [5 month-old, male, NIPPON CHARLES RIVER (KK)] stored frozen at −80° C. was thawed at room temperature and, after removing an unwanted fat adhering to the skin, cut into pieces, each in about 2 cm square, which were subjected to a permeation test.

In the permeation test, a diffusion cell of a modified Franz type (valid surface area: 1.1 $cm^2$, receptor phase: 16 ml) containing a phosphate buffer, pH7.1, was provided on the receptor phase side, which was stirred with a star-head magnet at 600 rpm with keeping at 37° C. On the donor side, 0.5 ml of a sample solution was contained and closed with a glass ball in order to prevent the evaporation of the sample solution. At a predetermined time, an aliquot was sampled and an equal volume of a buffer solution was supplemented. A receptor phase fractionated was subjected to a high pressure liquid chromatography (HPLC) to quantify the drug which had permeated. The permeation test was continued over a period of 30 to 48 hours.

(3) HPLC Conditions
  Instrument: SHIMADZU System Model LC-6A (SHIMADZU)
  Column: TSK-GEL ODS 120T 4.6 mm×150 mm (TOSO)
  Mobile phase: Determination of IM and promoting agent: Methanol:0.1% phosphoric acid=75:25
  Determination of ANP and promoting agent: Methanol:0.1% phosphoric acid=30:70
  Flow rate: 1.0 ml/min (4) Drug Detection
  IM and ANP were determined using an UV spectrophotometer model SPD-6A (SHIMADZU) at wavelengths of 254 nm and 245 nm, respectively.

(5) Data Processing
  Using CHROMATOPAK CR-4A (SHIMADZU), a calibration curve was made from the peak areas of each of IM and ANP, and used to calculate a concentration.

Results
(1) Dermal Permeation Test of IM
A curve of cumulative permeation vs time of each sample solution is shown in FIG. 1.

As evident from FIG. 1, MDM exhibited a dermal permeation-promoting ability which was not as high as that of LM but was higher than that of MPD.

In addition, MDM promoted the dermal permeation of IM which is a lipophilic agent.

(2) Dermal Permeation Test of ANP

Figure 2:
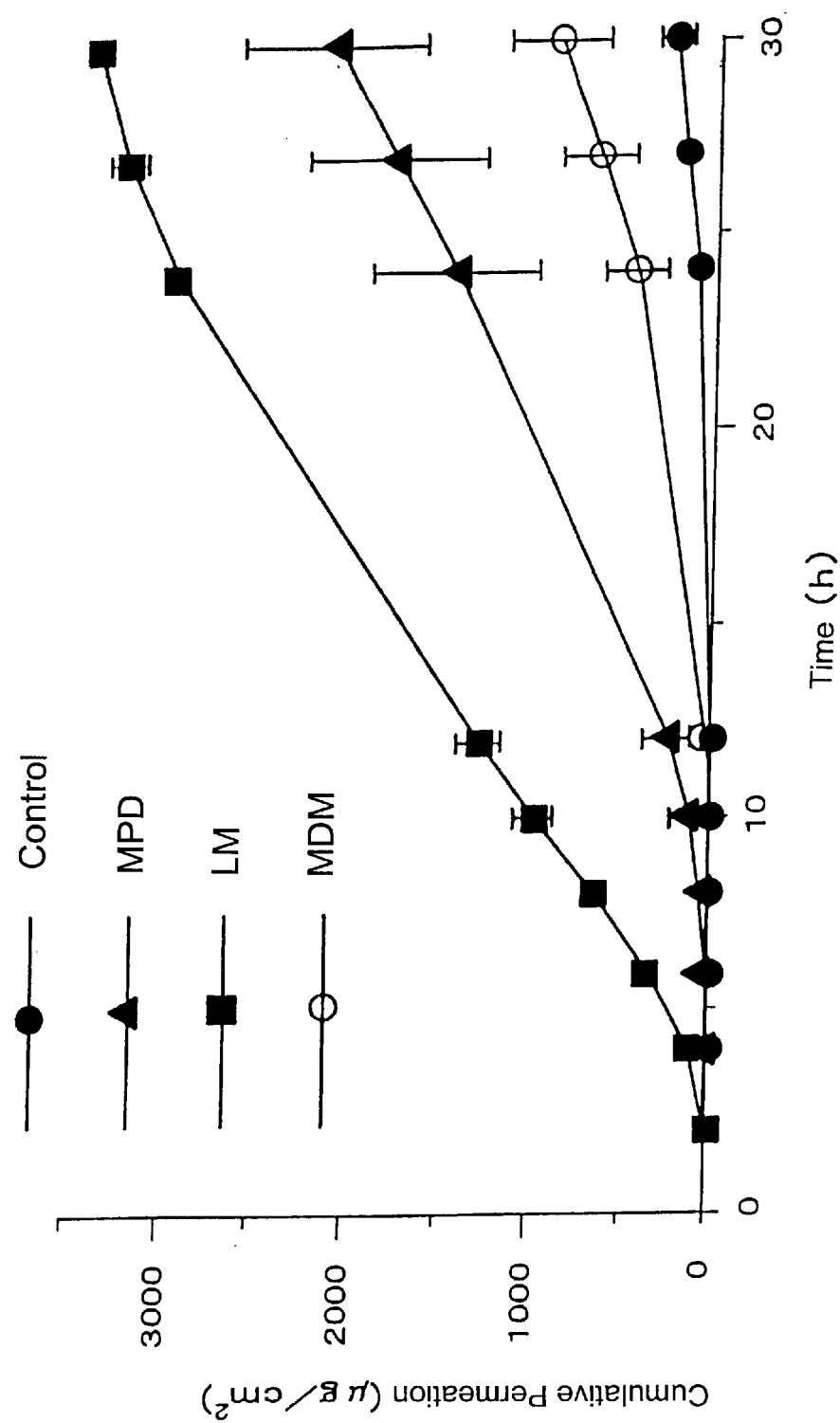
FIG. 2 shows the results of the dermal permeation test of antipyrine (ANP) in Example 1.

A curve of cumulative permeation vs time of each sample solution is shown in FIG. 2.

As evident from FIG. 2, MDM exhibited a dermal permeation-promoting ability, although the ability was not as high as that of LM and MPD.

In addition, MDM promoted the dermal permeation of ANP which is a hydrophilic agent.

Example 2

A lipophilic agent indomethacin (IM) was used to compare the dermal absorption-promoting effect of p-menthane-3,8-diol (MDM: mixture of trans and cis forms) with those of l-menthol (LM) together with a control.

A sample had a composition shown in Table 3 and was prepared similarly as in Example 1 except for using 1,3-butylene glycol (indicated as 1,3-BG in Table) instead of ethanol employed in the sample preparation in Example 1.

TABLE 3

|            | Control | MDM  | LM   |
| ---------- | ------- | ---- | ---- |
| Water (ml) | 6.0     | 6.0  | 6.0  |
| 1,3-BG (ml)| 4.0     | 4.0  | 4.0  |
| IM (g)     | 0.05    | 0.05 | 0.05 |
| MDM (g)    | —       | 0.3  | —    |
| LM (g)     | —       | —    | 0.3  |

Results

Figure 3:
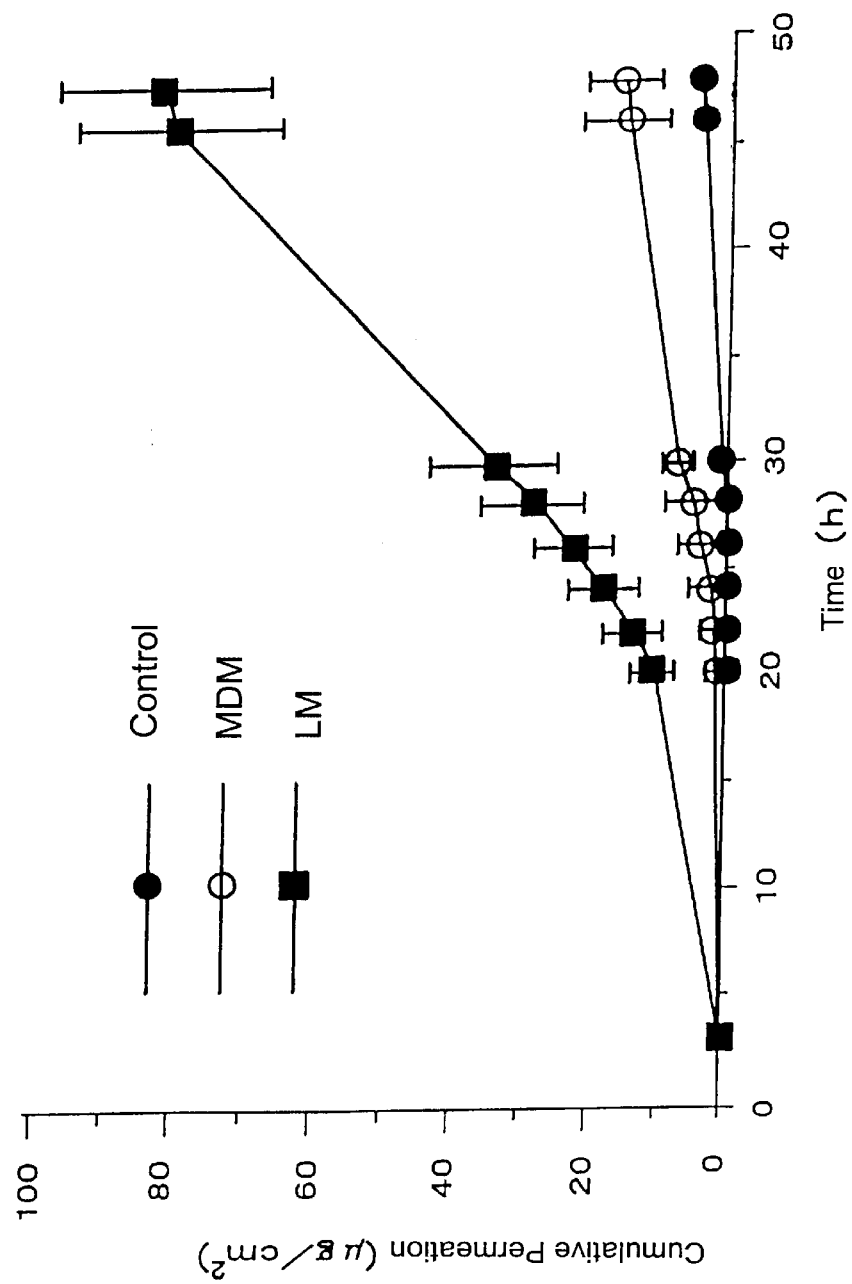
FIG. 3 shows the results of the dermal permeation test of IM in Example 2.

A curve of cumulative permeation vs time of each sample solution is shown in FIG. 3.

As evident from FIG. 3, MDM exhibited a dermal permeation-promoting ability, although the ability was not as high as that of LM.

In addition, MDM promoted the dermal permeation of IM which is a lipophilic agent.

Example 3

A lipophilic agent indomethacin (IM) was used to compare the dermal absorption-promoting effects of p-menthane-3,8-diol (MDM: mixture of trans and cis forms) alone and of a 1:1 (by weight) combination of p-menthane-3,8-diol (MDM: mixture of trans and cis forms) and 3-l-menthoxypropane-1,2-diol (MPD) with that of a control (containing no dermal absorption-promoting agent) and with that of 3-l-menthoxypropane-1,2-diol alone.

A sample had a composition shown in Table 4 and was prepared similarly as in Example 1 except for using 1,3-butylene glycol (indicated as 1,3-BG in Table 4) instead of ethanol employed in the sample preparation in Example 1.

TABLE 4

|             | Control | MDM  | MPD  | MDM + MPD |
| ----------- | ------- | ---- | ---- | --------- |
| Water (ml)  | 6.0     | 6.0  | 6.0  | 6.0       |
| 1,3-BG (ml) | 4.0     | 4.0  | 4.0  | 4.0       |
| IM (g)      | 0.05    | 0.05 | 0.05 | 0.05      |
| MDM (g)     | —       | 0.3  | —    | 0.15      |
| MPD (g)     | —       | —    | 0.3  | 0.15      |

Results

Figure 4:
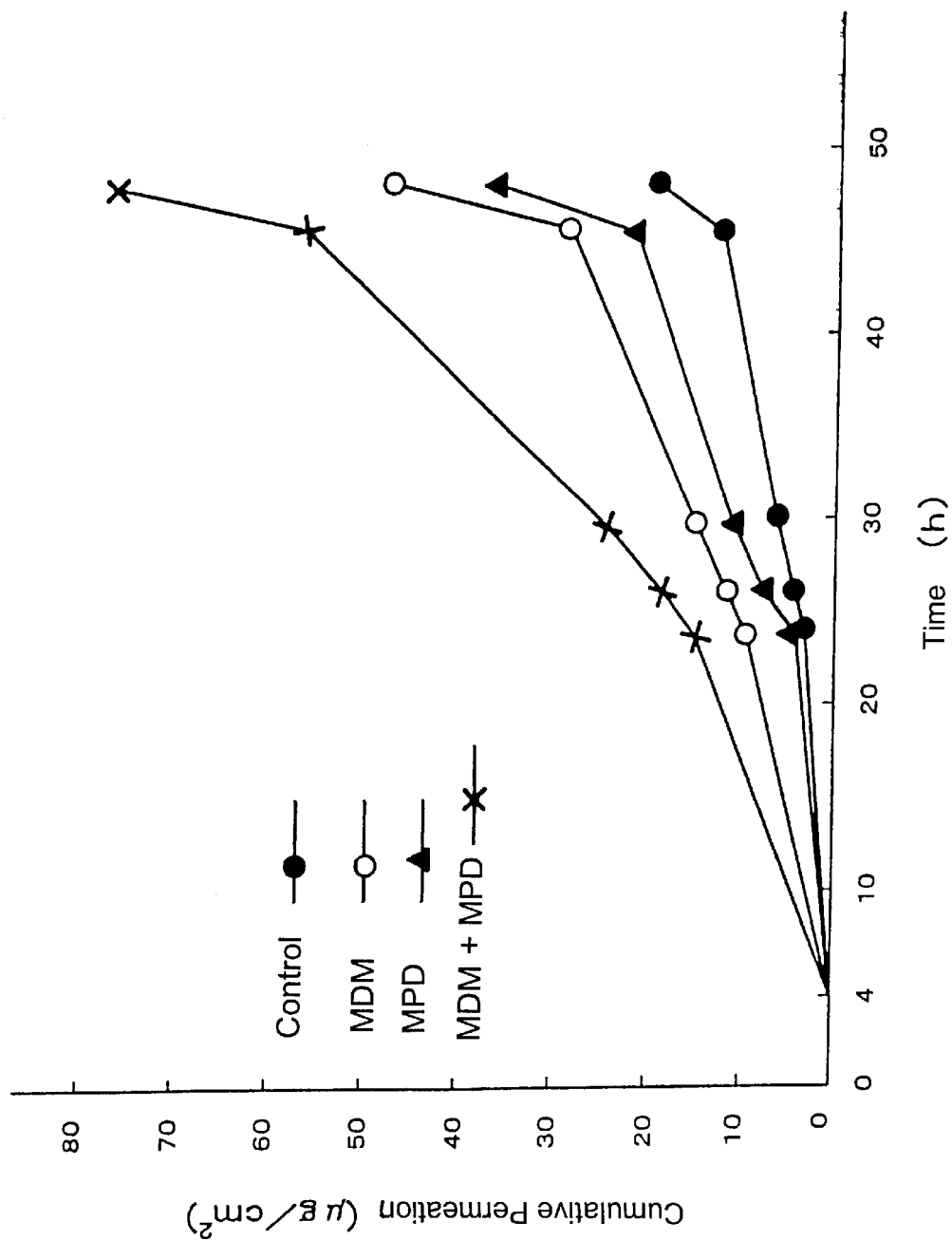
FIG. 4 shows the results of the dermal permeation test of IM in Example 3.

A curve of cumulative permeation vs time of each sample solution is shown in FIG. 4.

As evident from FIG. 4, MDM exhibited a dermal permeation-promoting ability higher than that of MPD.

In addition, the combination of MDM and MPD exhibited a dermal permeation-promoting ability far higher than that of MDM alone and of MPD alone.

As described above, p-menthane-3,8-diol according to the present invention promoted the dermal permeation of both of lipophilic agent indomethacin and hydrophilic antipyrine. A combination of p-menthane-3,8-diol and 3-l-menthoxy-1,2-propanediol had a dermal permeation-promoting effect higher than that of p-menthane-3,8-diol when used alone and that of 3-l-menthoxy-1,2-propanediol when used alone.

While the dermal permeation-promoting effect on indomethacin and antipyrine was somewhat lower than that of l-menthol having the same p-menthane backbone, a less expensive formulation can be achieved without exhibiting a too intense mint flavor characteristic of l-menthol and without a need of a complicated operation for masking the odor usually in preparing a topical formulation.

What is claimed is:

1. A dermal absorption-promoting agent consisting essentially of p-menthane-3,8-diol and 3-l-menthoxypropane-1,2-diol.

2. A topical formulation containing a dermal absorption-promoting agent consisting essentially of p-menthane-3,8-diol and 3-l-menthoxypropane-1,2-diol in combination with a drug suitable for dermal administration.

3. A dermal absorption-promoting agent comprising p-menthane-3,8-diol, 3-l-menthoxypropane-1,2-diol and 1,3-butylene glycol.

4. A topical formulation containing a dermal absorption-promoting agent consisting essentially of p-menthane-3,8-diol, 3-l-menthoxypropane-1,2-diol and 1,3-butylene glycol in combination with a drug suitable for dermal administration.

5. A dermal absorption-promoting agent according to claim 1 wherein p-menthane-3,8-diol and 3-l-menthoxypropane-1,2-diol are present in a ratio of 1:99 to 99:1 by weight.

6. A topical formulation according to claim 2 containing 0.1 to 50% by weight total of p-menthane-3,8-diol and 3-l-menthoxypropane-1,2-diol.

7. A dermal absorption-promoting agent according to claim 3 wherein p-menthane-3,8-diol and 3-l-menthoxypropane-1,2-diol are present in a ratio of 1:99 to 99:1 by weight.

8. A topical formulation according to claim 4 containing 0.1 to 50% by weight total of p-menthane-3,8-diol and 3-l-menthoxypropane-1,2-diol.

9. A topical formulation according to claim 4, wherein the drug suitable for dermal administration is an anti-inflammatory agent.

10. A topical formulation according to claim 9, wherein the anti-inflammatory agent is indomethacin, phenylbutazone, naproxen or ibuprofen.

11. A topical formulation according to claim 4, wherein the drug suitable for dermal administration is an antipyretic/analgesic.

12. A topical formulation according to claim 11, wherein the antipyretic/analgesic is antipyrine.

13. A topical formulation according to claim 2, wherein the drug suitable for dermal administration is an anti-inflammatory agent.

14. A topical formulation according to claim 13, wherein the anti-inflammatory agent is indomethacin, phenylbutazone, naproxen or ibuprofen.

15. A topical formulation according to claim 2, wherein the drug suitable for dermal administration is an antipyretic/analgesic.

16. A topical formulation according to claim 15, wherein the antipyretic/analgesic is antipyrine.

* * * * *

UNITED STATES PATENT AND TRADEMARK OFFICE
CERTIFICATE OF CORRECTION

PATENT NO.     : 6,410,034 B1
DATED          : June 25, 2002
INVENTOR(S)    : Mitsuo Matsumoto et al.

It is certified that error appears in the above-identified patent and that said Letters Patent is hereby corrected as shown below:

Title page,
Item [56], add to FOREIGN PATENT DOCUMENTS -- JP 11263701 A1 (ABSTRACT) * 9/1999 --

Signed and Sealed this

Nineteenth Day of November, 2002

Attest:

Attesting Officer

JAMES E. ROGAN
Director of the United States Patent and Trademark Office